(12) United States Patent
Park

(10) Patent No.: US 11,612,373 B2
(45) Date of Patent: Mar. 28, 2023

(54) IMAGE PROCESSING APPARATUS FOR C-ARM

(71) Applicant: Sang Ho Park, Seoul (KR)

(72) Inventor: Sang Ho Park, Seoul (KR)

( * ) Notice: Subject to any disclaimer, the term of this patent is extended or adjusted under 35 U.S.C. 154(b) by 27 days.

(21) Appl. No.: 17/320,857

(22) Filed: May 14, 2021

(65) Prior Publication Data
US 2021/0353242 A1    Nov. 18, 2021

(30) Foreign Application Priority Data

May 18, 2020  (KR) .................. 10-2020-0058998

(51) Int. Cl.
*A61B 6/00* (2006.01)
*A61B 6/04* (2006.01)
*A61B 6/08* (2006.01)

(52) U.S. Cl.
CPC .......... *A61B 6/5235* (2013.01); *A61B 6/0407* (2013.01); *A61B 6/08* (2013.01); *A61B 6/4441* (2013.01); *A61B 6/463* (2013.01); *A61B 6/467* (2013.01); *A61B 6/505* (2013.01); *A61B 6/54* (2013.01)

(58) Field of Classification Search
CPC ..... A61B 6/4441; A61B 6/5205; A61B 6/548; A61B 6/5235; A61B 6/505; A61B 6/467; A61B 6/407; A61B 6/08; A61B 6/463; A61B 6/54
See application file for complete search history.

(56) References Cited

U.S. PATENT DOCUMENTS

2015/0282776 A1* 10/2015 Shin ..................... A61B 6/5241
378/62

FOREIGN PATENT DOCUMENTS

KR      20150124262       11/2015

\* cited by examiner

*Primary Examiner* — Don K Wong
(74) *Attorney, Agent, or Firm* — Cantor Colburn LLP

(57) ABSTRACT

Provided is an image processing apparatus for a C-arm, including: a movement control unit which moves a C-arm which irradiates a radiation onto a bone of a subject located on a table and detects the radiation which penetrates the bone to generate a projection image for the bone, along a predetermined route; an image acquiring unit which acquires a plurality of projection images generated by the moving C-arm at every predetermined interval; and an image processing unit which generates a combined projection image in which the plurality of acquired projection images is combined, and the predetermined interval may be an interval at which a continuous panoramic image may be generated by connecting the plurality of acquired projection images.

8 Claims, 9 Drawing Sheets

(b)

IMAGE PROCESSING APPARATUS FOR C-ARM

BACKGROUND

Field

The present disclosure relates to an image processing apparatus for a C-arm, and more particularly, to an image processing apparatus for a C-arm which introduces a panoramic photographic technique to project multilevel spine images onto one screen during a spinal surgery using a C-arm.

Description of the Related Art

An X-ray imaging device is a device which irradiates an X-ray onto a subject and acquires internal images of the subject by using the X-ray which penetrates the subject. Since the transmittance of the X-ray varies depending on a characteristic of a material which configures a subject, an intensity or a strength of the X-ray which passes through the subject is detected to image an internal structure of the subject. Among the X-ray imaging devices, an X-ray device which is used in an X-ray room is a fixed type and an X-ray device which is used in an operating room is a mobile type.

A mobile X-ray device has a C-shape, so that it is called a C-arm or a C-type X-ray projection device. The C-arm is equipment which generates X-ray and processes an image using a computer to show the images as videos on a monitor in real time to align bones, or implant a screw or a pin during the operation of fracture patients, disk patients, or spine-related patients in an operating room of a hospital, or see the structure of the bone at various angles, or confirm whether the reposition is well done when the manual reposition (to align the bones without performing an operation) of the fracture is performed. Such a C-arm is equipment which is particularly necessary for orthopedic or neurosurgery and has a much better sharpness than a general X-ray device.

In the general X-ray imaging, the imaging is performed by adjusting a position of a portion of the patient to be imaged while fixing an X-ray sensor. In contrast, in the case of the C-arm, the imaging is performed by adjusting the position of the C-arm while fixing the patient on an operation table.

The C-arm may be referred to as a mobile X-ray device for surgical operation which may fluoroscopically scan the presence, the size, and the position of lesions during spinal canal stenosis, joint syndrome after spinal surgery, or various disk surgeries.

FIG. 1 is a view illustrating a configuration of a general C-arm and FIG. 2 is a view illustrating an example of a projection image acquired by the C-arm. Specifically, FIG. 2 illustrates an example of a projection image for a part of a spine of a subject.

Referring to FIGS. 1 and 2, generally, the C-arm continuously radiates X-rays generated using a radiation generating device to digitize the result using a charge coupled device (CCD) camera and output the digitized result on a monitor and store a data value in a computer.

The C-arm shows an image projected onto a detector (a radiation detector) with a size of approximately 9 inches so that for example, as illustrated in FIG. 2, an image for a structure which is narrow and has a limited size may be obtained.

Generally, in the orthopedic surgery of fractures of limb joints or limb bones, it does not matter to observe only a narrow area based on a C-arm image which is a projection image acquired by the C-arm. However, when a multilevel spinal surgery is performed, an angle of the spine needs to be measured or a target position of a spine needs to be checked while watching the entire spine through one screen in some cases. However, there is a problem in that such desired information cannot be obtained using a general C-arm image.

In other words, during the multilevel spinal surgery, in some cases, it is necessary to check an angle of the entire spine or a desired position of the spine so that a full spine image which allows the observation of the entire spine is required. However, it is not possible to observe the entire spine by images (C-arm images of the related art which are images in a limited area of approximately 9 inches) acquired by the C-arm of the related art so that information such as an angle of the entire spine cannot be obtained.

Currently, the multilevel image cannot be obtained during the surgery so that the surgery result needs to be checked by re-imaging in the radiology department after the surgery. Therefore, there is a serious problem in that even though a problem is found, the problem cannot be immediately solved. Accordingly, an operating surgeon is very anxious because an exact situation cannot be identified until the operating surgeon checks the image result obtained by re-examination in the radiology department after the surgery. Further, the patient has no choice but to take the risk for a problem which is not recognized during the surgery.

In other words, currently, there is no technique suitable to acquire multilevel images during the surgery and according to the related art, in order to confirm whether the surgery is well done, the imaging is performed again in the radiology department after the surgery and the surgery result is checked based on the re-captured images. Therefore, the operating surgeon is very anxious because the surgeon cannot confirm whether the surgery is well done until the surgeon checks the recaptured image. Further, since it is difficult to acquire the multilevel images during the surgery, even though problems occur during the surgery, the problems cannot be immediately solved so that in some cases, reoperation needs to be performed under the general anesthesia.

Further, according to the related art, when a C-arm image for an entire spine needs to be acquired, a user must repeatedly perform a number of imaging while counting the segments of the subject's spine from bottom to top one by one, which may cause the inconvenience of the user and increase the risk of the radiation exposure.

Furthermore, according to the related art, an operator acquires C-arm images while manually moving the position of the C-arm so that a large overlapping image between a plurality of acquired images is generated to acquire an unnecessary image or two images do not overlap to generate a bone portion which is not checked by the images. In this case, the re-imaging is necessary to acquire the C-arm image again, which may cause a problem in that the radiation exposure (radiation dose) to the subject is increased and the operating hours are delayed.

Therefore, it is required to develop a technology which immediately finds out the problem during the multilevel spinal surgery in the operating room to correct the problem.

A related art of the present disclosure is disclosed in Korean Unexamined Patent Application Publication No. 10-2015-0124262.

SUMMARY

The present disclosure is made to solve the above-described problems of the related art and an object thereof is to provide an image processing apparatus for a C-arm which solves the problem in that the entire spine cannot be observed from an image acquired by the C-arm of the related art due to the limited sensor size so that a shape or an angle of the entire spine cannot be checked.

The present disclosure is made to solve the above-described problems of the related art and an object thereof is to provide an image processing apparatus for a C-arm which solves the problem in that the multilevel images cannot be obtained during the surgery in the related art so that the imaging is performed again in the radiology department after the surgery to check the surgery result and thus the operating surgeon has to be very anxiety for several hours until the operating surgeon checks the image result obtained by reexamination by the radiology department after the surgery and resolves the risk of the reoperation of the patient.

Further, the present disclosure is made to solve the above-described problems of the related art and an object thereof is to provide an image processing apparatus for a C-arm which is capable of acquiring a multilevel image during the surgery, improving the convenience of the operator, minimizing a radiation exposure to the subject, and shortening the operating hours.

An object of the present disclosure is to provide an image processing apparatus for a C-arm which is capable of immediately finding out the problem generated during the multilevel spinal surgery in the operating room to correct the problem.

However, objects to be achieved by various embodiments of the present disclosure are not limited to the technical objects as described above and other technical objects may be present.

As a technical means to achieve the above-described technical object, according to a first aspect of the present disclosure, an image processing apparatus for a C-arm includes: a movement control unit which moves a C-arm which irradiates a radiation onto a bone of a subject located on a table and detects the radiation which penetrates the bone to generate a projection image for the bone, along a predetermined route; an image acquiring unit which acquires a plurality of projection images generated by the moving C-arm at every predetermined interval; and an image processing unit which generates a combined projection image in which the plurality of acquired projection images is combined, and the predetermined interval may be an interval at which a continuous panoramic image may be generated by connecting the plurality of projection images acquired from the C-arm.

As a technical means to achieve the above-described technical object, according to a second aspect of the present disclosure, a control method of an image processing apparatus for a C-arm is a method for controlling an image processing apparatus for a C-arm according to the above-described first aspect including: (a) moving a C-arm which irradiates a radiation onto a bone of a subject located on a table and detects the radiation which penetrates the bone to generate a projection image for the bone, along a predetermined route by a movement control unit; (b) acquiring a plurality of projection images generated by the moving C-arm at every predetermined interval by an image acquiring unit; and (c) generating a combined projection image in which the plurality of acquired projection images is combined, by an image processing unit, and the predetermined interval may be an interval at which a continuous panoramic image may be generated by connecting the plurality of projection images acquired from the C-arm.

The above-described solving means are merely illustrative but should not be construed as limiting the present disclosure. In addition to the above-described embodiments, additional embodiments may be further provided in the drawings and the detailed description of the present disclosure.

According to the aspect of the present disclosure, a combined projection image is provided by the image processing apparatus for a C-arm to solve the problem of the image acquired by the C-arm of the related art in that the full spine observation is not possible due to the limited sensor size so that a shape or an angle of the entire spine cannot be checked. That is, according to the present disclosure, a combined projection image is provided so that the multilevel spine image is projected onto one screen to be displayed during the spinal surgery using the C-arm.

According to the aspect of the present disclosure, the image processing apparatus for a C-arm is provided so that a multilevel image is obtained during the surgery. Therefore, it is possible to solve the problem of the related art in that the re-imaging is performed in the radiology department after the surgery to check the surgery result so that the operating surgeon is very anxiety until the operating surgeon checks the image result obtained by the reexamination by the radiology department after the surgery.

According to the aspect of the present disclosure, the image processing apparatus for a C-arm is provided so that the convenience of the operator is improved, the radiation exposure to the subject is minimized, and the operating hours are shortened.

According to the aspect of the present disclosure, the image processing apparatus for a C-arm is provided so that the problems generated during the multilevel spinal surgery are immediately checked in the operating room to be corrected and the risk of the patient accompanied by the reoperation may also be solved.

However, the effect which may be achieved by the present disclosure is not limited to the above-described effects, there may be another effects.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
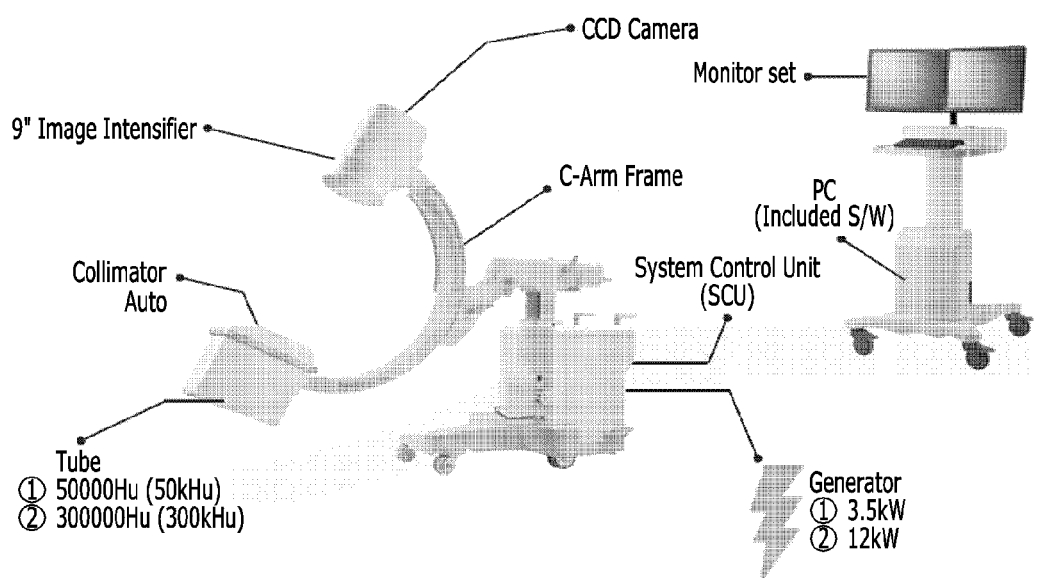
FIG. 1 is a view illustrating a configuration of a general C-arm.
Figure 2:
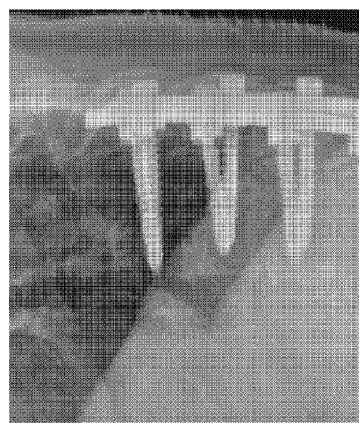
FIG. 2 is a view illustrating an example of a projection image acquired by the C-arm.

Hereinafter, the present disclosure will be described more fully hereinafter with reference to the accompanying drawings, in which exemplary embodiments of the present disclosure are shown. However, the present disclosure may be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

Figure 3:
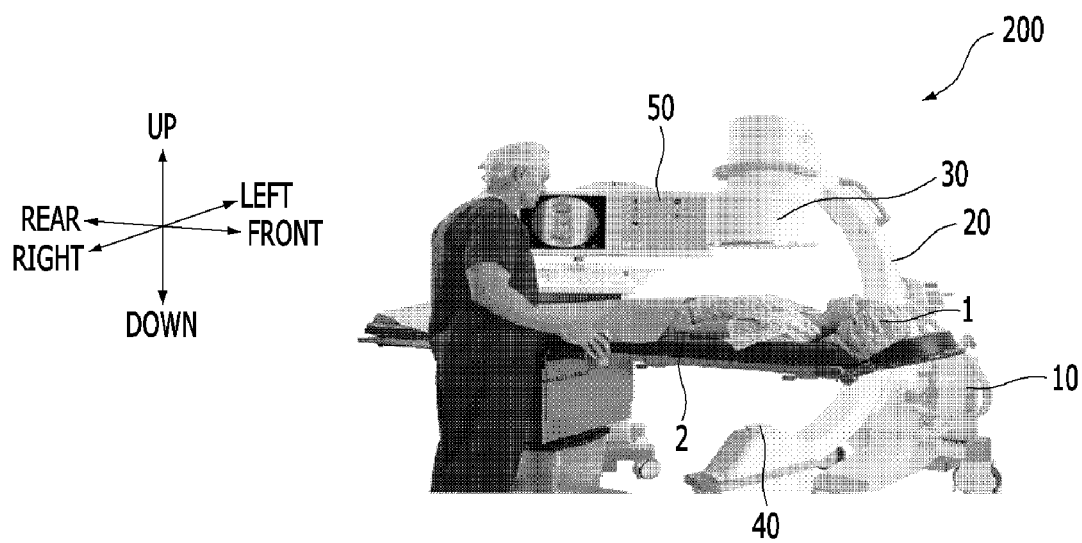
FIG. 3 is a view illustrating an example of a C-arm applied to an image processing apparatus for a C-arm according to an exemplary embodiment of the present disclosure.
Figure 4:
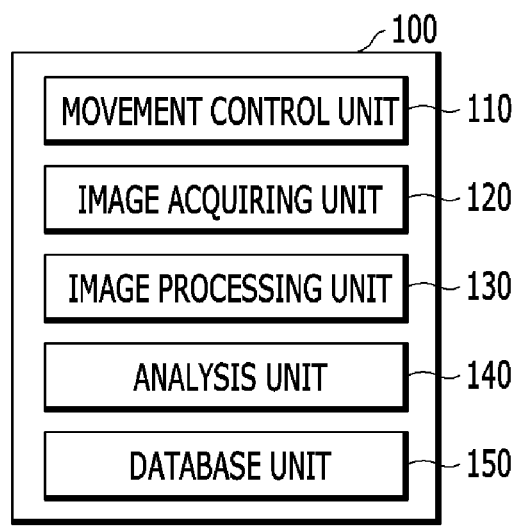
FIG. 4 is a block diagram illustrating a schematic configuration of an image processing apparatus for a C-arm according to an exemplary embodiment of the present disclosure.

FIG. 3 is a view illustrating an example of a C-arm 200 applied to an image processing apparatus for a C-arm according to an exemplary embodiment of the present disclosure. FIG. 4 is a block diagram illustrating a schematic configuration of an image processing apparatus 100 for a C-arm according to an exemplary embodiment of the present disclosure.

Hereinafter, the image processing apparatus 100 for a C-arm according to an exemplary embodiment of the present disclosure will be simply referred to as the present apparatus 100 for the convenience of description.

Further, in the following description of the present apparatus 100 and the C-arm 200, with respect to the drawing of FIG. 3, a 4 o'clock to 10 o'clock direction is referred to as a front and rear direction, a 2 o'clock to 8 o'clock direction is referred to as a left and right direction, and a 12 o'clock to 6 o'clock direction is referred to as a up and down direction. However, such direction setting is merely an example for better understanding of the present disclosure, so that it is not limited thereto. Further, in the following description, the radiation and the X-ray may refer to the same configuration.

Referring to FIGS. 3 and 4, the C-arm 200 considered in the present apparatus 100 may also referred to as a mobile X-ray imaging device, a C-type X-ray system, or a mobile C-arm fluoroscopy.

In the C-arm 200 considered in the present apparatus 100, a configuration of the C-arm known in the related art or various configurations of C-arm which will be developed in the future may be applied. Hereinafter, the detailed description of a structure, a configuration, and an operation principle of the C-arm will be omitted.

The configuration of the C-arm 200 will be briefly described with reference to FIG. 3. The C-arm 200 may include a main body 10, a C-arm frame 20, a radiation generator 30, a radiation detector 40, and a display unit 50. The radiation generator 30 may also be referred to as a radiation generating unit or an X-ray generator and the radiation detector 40 may also be referred to as a radiation detecting unit.

The C-arm 200 allows an irradiation range of the radiation (X-ray) to be displayed on a subject 1 when the subject is scanned in various locations such as an examination room, an emergency room, an X-ray room, a pain treatment room, and an operating room to allow an operator to avoid the radiation irradiation range.

In the main body 10, a lifting unit (not illustrated) and control devices are disposed and a plurality of casters may be disposed on a lower surface of the main body 10 for the convenience of the movement.

The C-arm frame 20 is connected to the lifting unit and may move in the up and down direction and the left and right direction with respect to the lifting unit. For example, the up and down direction with respect to the lifting unit refers to a up and down direction corresponding to the 12 o'clock to 6 o'clock with respect to the drawing of FIG. 3 and the left and right direction with respect to the lifting unit refers to a front and rear direction corresponding to the 4 o'clock to 10 o'clock with respect to the drawing of FIG. 3.

In addition, the C-arm frame 20 may move to be rotatable in a clockwise or counterclockwise direction around a table 2 when the table 2 is viewed from the front as an example in the drawing of FIG. 3.

As seen from the front side, the C-arm frame 20 may be formed to have a C-shape. One end and the other end of the C-arm frame 20 may be spaced apart from each other to be opposite to each other with the table 2 on which the subject 1 is located, therebetween.

For example, the subject 1 may be a person (human). However, the subject is not limited thereto and as the subject 1, a living body such as an animal and any object whose inside may be imaged by the radiation (X-ray) may be applied.

The radiation generator 20 may be disposed at one end of the C-arm frame 20 to be connected to the C-arm frame 20. The radiation generator 30 generates radiation (X-ray) and may irradiate the radiation to the subject 1 to acquire a radiation (X-ray) image of the subject 1.

The radiation detector 40 may be disposed at the other end of the C-arm frame 20 to be connected to the C-arm frame 20. The radiation detector 40 may be disposed at the other end of the C-arm frame 20 to be opposite to the radiation generator 30 with the subject 1 located on the table 2 therebetween.

The radiation detector 40 may detect radiation which penetrates the subject 1. That is, the radiation detector 40 may detect radiation (radiation which penetrates the subject) as the radiation which is irradiated onto the subject 1 by the radiation generator 30 penetrates the subject 1. The radiation detector 40 detects the penetrating radiation and converts the detected radiation into radiation (X-ray) data which is an electric signal.

In other words, the C-arm 200 irradiates radiation onto a bone of the subject 1 located on the table 2 and detects radiation which penetrates the bone to generate a projection image for the bone. Here, the projection image may also be represented as a C-arm image, a radiation (X-ray) image, or the like.

Specifically, the radiation generator 30 may irradiate the radiation toward the bone in the body of the subject 1 located on the table 2. The radiation generator 30 may generate the radiation and irradiate the generated radiation toward the bone in the body.

The radiation detector 40 is located at the opposite side of the radiation generator 30 with the bone in the body of the subject 1 therebetween and acquires a projection image (fluoroscopic image) for the bone in the body of the subject 1 by detecting the radiation which penetrates the bone in the body. In other words, the radiation detector 40 detects the radiation which penetrates the bone of the subject 1 to generate a projection image for the bone.

The radiation detector 40 may include a sensor (not illustrates) which senses the radiation penetrating the bone. The sensor (not illustrated) may be provided at an end portion of the radiation detector 40 which faces the radiation generator 30.

The display unit 50 receives the projection image generated by the radiation detector 40 from the radiation detector 40 and may display the received projection image to the outside by means of a screen.

Hereinafter, the present apparatus 100 will be described in detail based on the above description of the C-arm 200.

The present apparatus 100 is an image processing apparatus for a C-arm and for example, may be provided to be built in the main body 10 of the C-arm 200. However, it is not limited thereto, but the present apparatus 100 may be provided to be separated from the C-arm 200.

The present apparatus 100 and the C-arm 200 may be connected via a network and thus the present apparatus 100 may control various operations of the C-arm 200.

Examples of a network which is applicable between the present apparatus 100 and the C-arm 200 may include a 3$^{rd}$ generation partnership project (3GPP) network, a long term evolution (LTE) network, a world interoperability for microwave access (WIMAX) network, Internet, a local area network (LAN), a wireless local area network (wireless LAN), a wide area network (WAN), a personal area network (PAN), a Bluetooth network, a near field communication (NFC) network, a satellite broadcasting network, an analog broadcasting network, a digital multimedia broadcasting (DMB) network, and the like. However, the network is not limited thereto and various wired/wireless networks may be applied.

The present apparatus 100 may include a movement control unit 110, an image acquiring unit 120, an image processing unit 130, and an analysis unit 140.

The movement control unit 110 may control the movement of the C-arm 200. In other words, the movement control unit 110 may move the C-arm 200 which irradiates radiation onto a bone of the subject 1 located on the table 2 and detects radiation which penetrates the bone to generate a projection image for the bone, along a predetermined route.

The image acquiring unit 120 may acquire a plurality of projection images which is generated at a predetermined interval by the C-arm 200 which moves along the predetermined route, from the C-arm 200.

That is, the C-arm 200 may irradiate the radiation at every predetermined interval while moving along the predetermined route in response to the movement control by the movement control unit 110 of the present apparatus 100 and generate the projection image at every predetermined interval in response thereto. By doing this, the C-arm 200 generates a projection image at every predetermined interval while moving along the predetermined route to generate a plurality of projection images while moving the predetermined route.

The C-arm 200 may transmit (provide) the plurality of generated projection images to the image acquiring unit 120 of the present apparatus 100 via a network and the image acquiring unit 120 may acquire a plurality of projection images from the C-arm 200 therethrough.

Whenever the projection image is generated, the C-arm 200 may transmit the projection image to the image acquiring unit 120. That is, the C-arm 200 may transmit a projection image to the image acquiring unit 120 as soon as one projection image is generated. By doing this, the image acquiring unit 120 may sequentially acquire the projection images generated by the C-arm 200 at every predetermined interval, from the C-arm 200 which moves along the predetermined route.

At this time, the predetermined interval may refer to an interval at which the C-arm 200 generates the projection image or an interval at which the image acquiring unit 120 acquires the projection image from the C-arm 200.

Such a predetermined interval may be an interval at which the image acquiring unit 120 may connect the plurality of projection images acquired from the C-arm 200 to generate a continuous panoramic image. Here, the continuous panoramic image may refer to a linear panoramic image.

Further, the predetermined interval may refer to a predetermined time interval or a predetermined distance interval.

Furthermore, the predetermined route may refer to a route which is set to move the C-arm 200 along the front and rear direction of the table 2. Specifically, the predetermined route may be a linear route which is set to linearly move the C-arm 200 along the front and rear direction of the table 2 as an example.

In other words, for example, the predetermined route may refer to a linear route which is set to move the C-arm 200 to be horizontal with the table 2 along the front and rear direction of the table 2 to acquire a continuous (linear) panoramic image.

The image processing unit 130 may generate a combined projection image obtained by combining a plurality of projection images acquired by the image acquiring unit 120 as a single image.

The image processing unit 130 may generate a combined projection image combined by connecting the plurality of projection images as one, by applying, for example, a feature point matching technique or an image stitching technique to the plurality of acquired projection images. Such a combined projection image is a continuous (linear) panoramic image and is also referred to as a linear panoramic projection image.

A size of the projection image acquired by the image acquiring unit 120 (that is, a size of each of the plurality of projection images) may be determined by the size of the radiation detector 40 which is provided at the other end of the C-arm 200 to detect the radiation which penetrates the bone. Specifically, the size of the projection image may be determined by the size of the sensor which is provided in the radiation detector 40 to sense the radiation.

Generally, the size of the radiation detector 40 used for the C-arm 200 may be 9 inches or 12 inches. Accordingly, the size of each of the projection images generated by the radiation detector 40 of the C-arm 200 may be 9 inches (or 12 inches).

In contrast, the combined projection image generated by the image processing unit 130 is obtained by combining the plurality of projection images as a single image so that the combined projection image may be larger than the size (for example, 9 inches) of each of the plurality of projection images.

Further, the bone of the subject 1 onto which the radiation is irradiated by the C-arm 200 may refer to a vertebra of the subject 1. However, it is not limited thereto so that the bone of the subject 1 may be bones of various portions in the body of the subject 1.

When the bone of the subject 1 onto which the radiation is irradiated is a bone (vertebra) corresponding to a spine of the subject 1, each of the plurality of projection images acquired by the image acquiring unit 120 is an image including a partial spinal portion of the entire spine of the subject 1 and the combined projection image generated by the image processing unit 130 may be an image including the entire spine of the subject 1.

Figure 5:
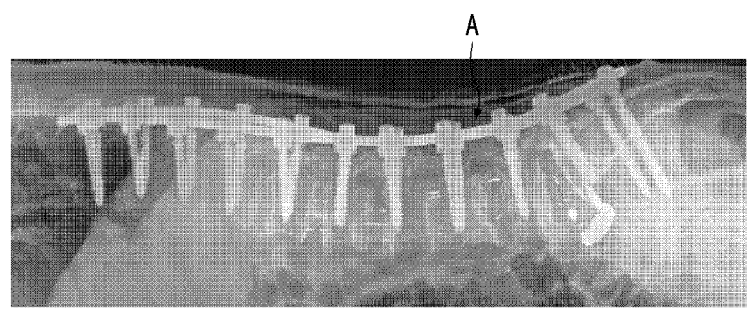
FIG. 5 illustrates an example of a radiation projection image of a spine surgical site for the instrumentation surgery.
Figure 6:
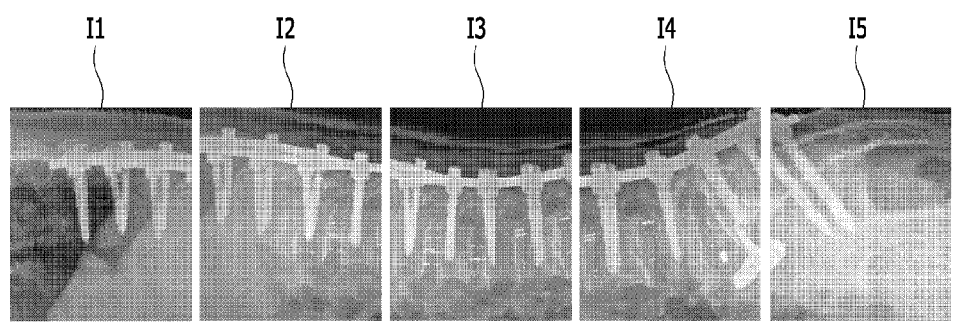
FIG. 6 is a view illustrating an example that a plurality of projection images for a spine surgical site illustrated in FIG. 5 is acquired by a C-arm of the related art.
Figure 7:
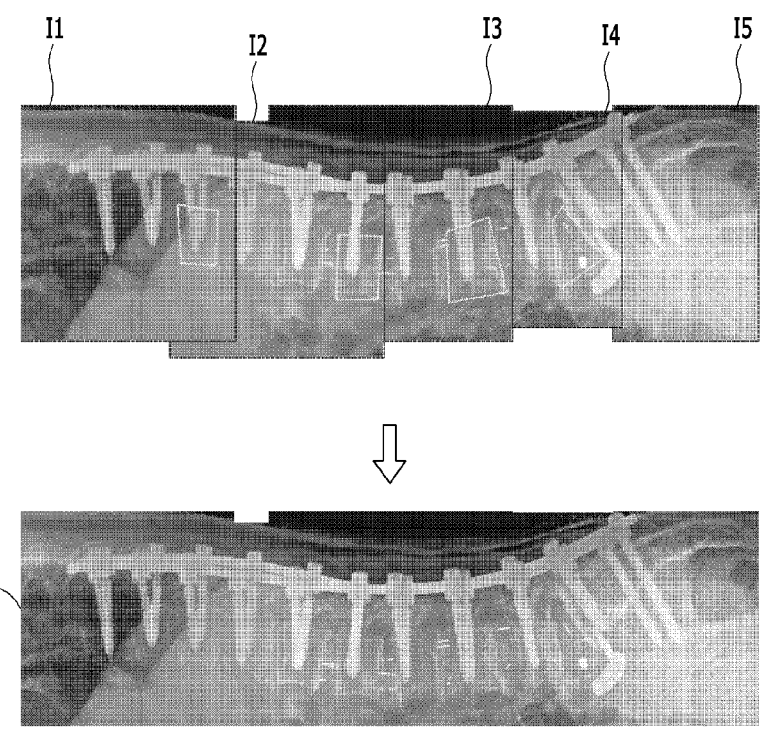
FIG. 7 is a view for explaining a process of generating a combined projection image by combining a plurality of projection images in an image processing apparatus for a C-arm according to an exemplary embodiment of the present disclosure.

FIG. 5 illustrates an example of a radiation projection image of a spine surgical site A for the instrumentation surgery. FIG. 6 is a view illustrating an example that a plurality of projection images I1, I2, I3, I4, and I5 for a spine surgical site A illustrated in FIG. 5 is acquired by a C-arm of the related art. FIG. 7 is a view for explaining a process of generating a combined projection image T1 by combining a plurality of projection images I1, I2, I3, I4, and I5 in an image processing apparatus 100 for a C-arm according to an exemplary embodiment of the present disclosure.

At this time, in FIG. 5, the spine surgical site A may refer to a vertebral portion corresponding to a ninth thoracic vertebra to a pelvic bone as an example of bones in the body of the subject 1.

Referring to FIGS. 5 to 7, for example, as illustrated in FIG. 5, the instrumentation surgery will be performed on the vertebral portion (spine surgical site A) corresponding to the ninth thoracic vertebra to the pelvic bone.

At this time, when the corresponding spine surgical site A is scanned using the C-arm of the related art, the size of the image acquired by the C-arm of the related art is limited (for example, it is limited to approximately 9 inches) so that there was no choice but to obtain fragmentary images as illustrated in FIG. 6. Accordingly, it is difficult to grasp the overall multilevel spinal surgery result using the C-arm of the related art.

In other words, FIG. 6 illustrates an example of a plurality of projection images I1, I2, I3, I4, and I5 generated by the C-arm by imaging the spine surgical site A illustrated in FIG. 5 with the C-arm of the related art. In other words, the plurality of projection images I1, I2, I3, I4, and I5 acquired by the image acquiring unit 120 from the C-arm 200 is as illustrated in FIG. 6 as an example.

By doing this, when the images I1, I2, I3, I4, and I5 acquired by the C-arm of the related art are used, it is difficult to entirely check (grasp) the multilevel spinal surgery result corresponding to the entire spine surgical site A due to the limited image size (9 inches) of the C-arm of the related art.

Therefore, the present apparatus 100 grafts a panoramic photographic technique (specifically, a linear panoramic photographic technique) onto the C-arm 200 of the related art to combine the plurality of projection images as a single projection image (a combined projection image) to enable the full checking of the entire spine surgical site A.

Specifically, referring to FIG. 7, the image processing unit 130 of the present apparatus 100 checks starting points of all of a plurality of single level images (that is, a plurality of projection images) I1, I2, I3, I4, and I5 scanned by the C-arm 200 using a panoramic photographic technique, using various image composite programs which has been known in the related art or will be developed in the future and overlaps and combines the single level images based on the starting points.

By doing this, the image processing unit 130 may generate a single combined projection image T1 obtained by entirely connecting the plurality of single level images (that is, a plurality of projection images) I1, I2, I3, I4, and I5. That is, the image processing unit 130 may generate a single combined projection image T1 obtained by combining the plurality of projection images I1, I2, I3, I4, and I5 acquired from the C-arm 200 as a single image. In the combined projection image T1, the entire spine (a spine surgical site A) corresponding to the ninth thoracic vertebrae to the pelvic bone may be represented.

That is, the image processing unit 130 checks the starting points of all the photographs of the plurality of projection images acquired from the C-arm 200 using the image composite program and overlaps and combines the projection images based on the starting points to generate a combined projection image as a single projection image obtained by entirely connecting the plurality of projection images as one. Such a combined projection image may be referred to as a continuous (linear) panoramic image.

Figure 8A:
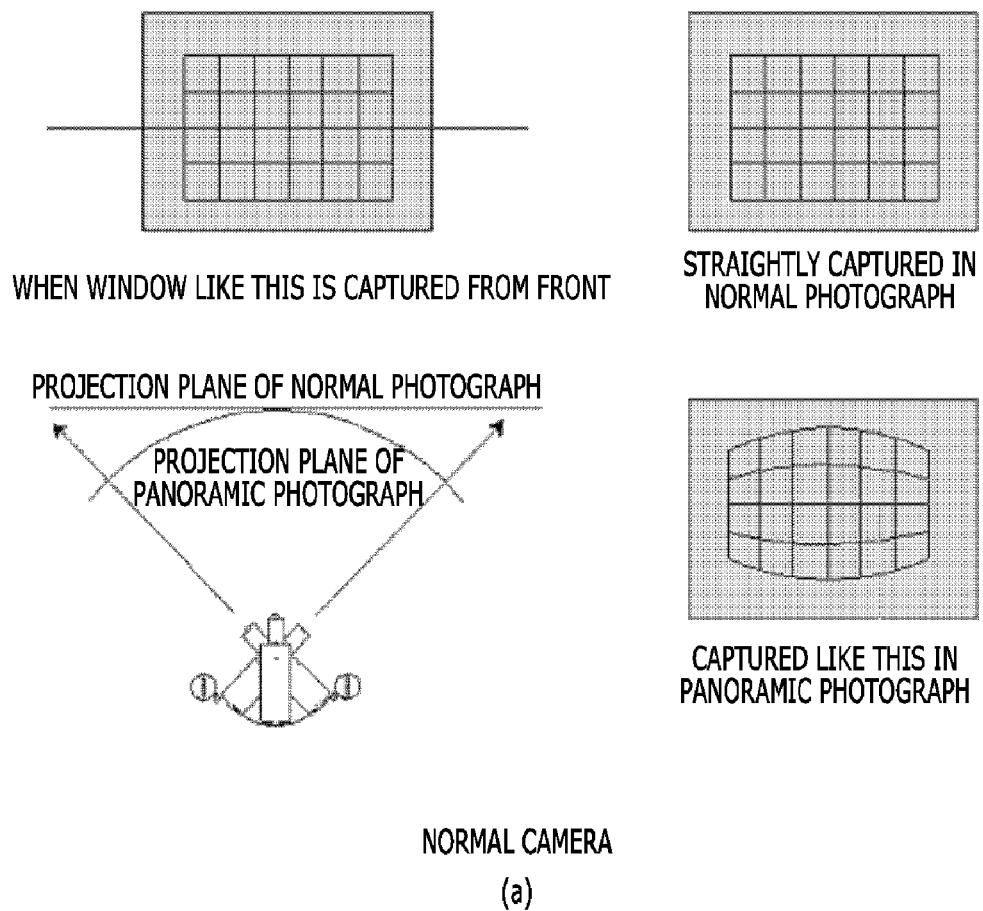
FIG. 8A is a view for explaining an example for controlling a camera to acquire a normal panoramic image and FIG. 8B is a view for explaining an example for controlling movement of a C-arm to generate a combined projection image which is a continuous panoramic image generated by an image processing apparatus for a C-arm according to an exemplary embodiment of the present disclosure.
Figure 8B:
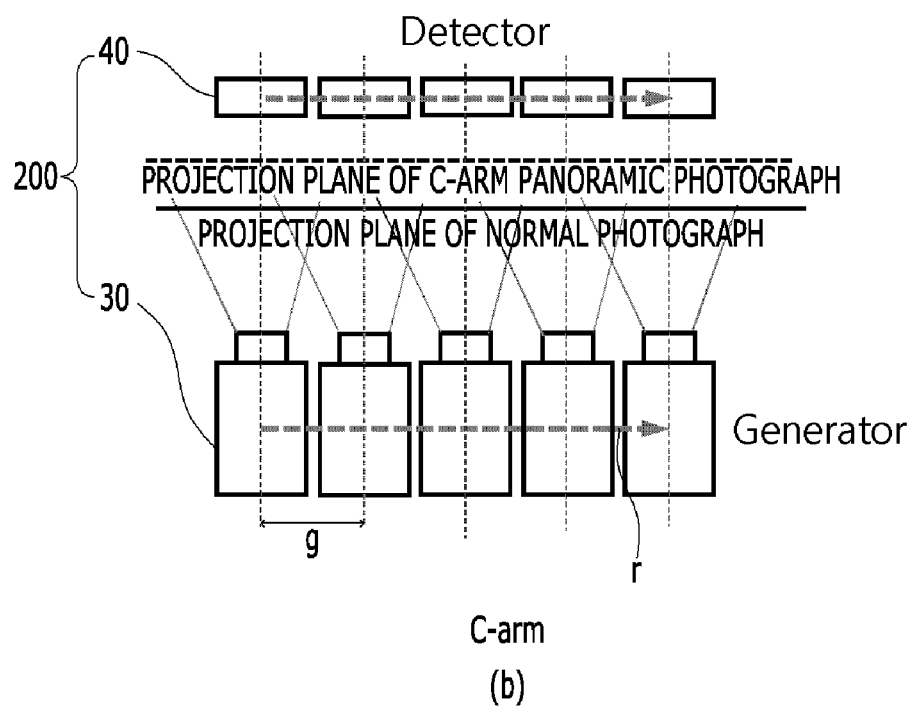

FIG. 8A is a view for explaining an example for controlling a camera to acquire a normal panoramic image and FIG. 8B is a view for explaining an example for controlling a movement of a C-arm 200 to generate a combined projection image which is a continuous (linear) panoramic image generated by an image processing apparatus 100 for a C-arm according to an exemplary embodiment of the present disclosure.

Referring to FIGS. 8A and 8B, according to the normal panoramic image acquiring technique, as illustrated in FIG. 8A, a plurality of cameras is circularly disposed with an interval and the images are cylindrically captured by the plurality of cameras. Thereafter, according to the normal panoramic image acquiring technique, the images acquired by the plurality of cameras are combined in a curved shape so that there is a problem in that a distortion occurs in the combined image. The distortion in the combined image causes the inaccuracy of the image so that when the corresponding image is utilized as a surgical image, there may be a difficulty in the surgery and it may lead to very fatal results.

In contrast, as illustrated in FIG. 8B, the movement control unit 110 of the present apparatus 100 may move the C-arm 200 along a linear route r which follows a front and rear direction of the table 2, as a predetermined route r, to be horizontal with a top surface of the table 2. The image acquiring unit 120 may acquire a plurality of projection images from the C-arm 200 which moves along the linear route.

At this time, when the movement control unit 110 moves the C-arm 200 along the predetermined route r, for example, the movement control unit 110 may control only the C-arm frame 20 to be moved while fixing the main body 10 of the C-arm 200. In accordance with the movement of the C-arm frame 20, the radiation generator 30 and the radiation detector 40 provided at both ends of the C-arm frame 20 also move together.

However, the present disclosure is not limited only thereto, but as another example, when the movement control unit 110 moves the C-arm 200 along the predetermined route r, the movement control unit 110 may move the entire main body 10 coupled to the C-arm frame 20. In accordance with the movement of the main body 10, the radiation generator 30 and the radiation detector 40 provided at both ends of the C-arm frame 20 also move together.

In the description of the present apparatus 100, when the movement control unit 110 moves the C-arm 200 along the predetermined route, it means that the C-arm frame 20 of the C-arm 200 is moved along the predetermined route and as a result, it means that the radiation generator 30 and the radiation detector 40 provided at both ends of the C-arm frame 20 are controlled to be moved.

The C-arm 200 may generate the projection image at every predetermined interval g by irradiating the radiation at every predetermined interval g while moving along the predetermined route r. The image acquiring unit 120 may acquire the plurality of projection images (that is, a plurality of projection images generated at every predetermined interval) generated by the C-arm 200 while moving along the predetermined route r, from the C-arm 200.

Thereafter, the image processing unit 130 combines the plurality of projection images acquired as the C-arm 200 linearly moves to generate a combined projection image T1 as a linear panoramic image which is a single image.

That is, in the normal panoramic image, a distortion is caused when the acquired images are combined. In contrast, the present apparatus 100 acquires a plurality of projection images while linearly moving the C-arm 200 to be horizontal with the table 2 and combines the images so that the distortion generated when the images are combined may be effectively reduced.

In the meantime, the analysis unit 140 may analyze physical feature information of the subject 1 located on the table 2.

At this time, the predetermined route may vary depending on the physical feature information of the subject 1 which is analyzed by the analysis unit 140. That is, the predetermined route may be set to be different for every subject 1, in accordance with the physical feature information of each subject 1. Here, the physical feature information may include information about a length of the spine and information about a shape of the spine, which will be described below.

Figure 9:
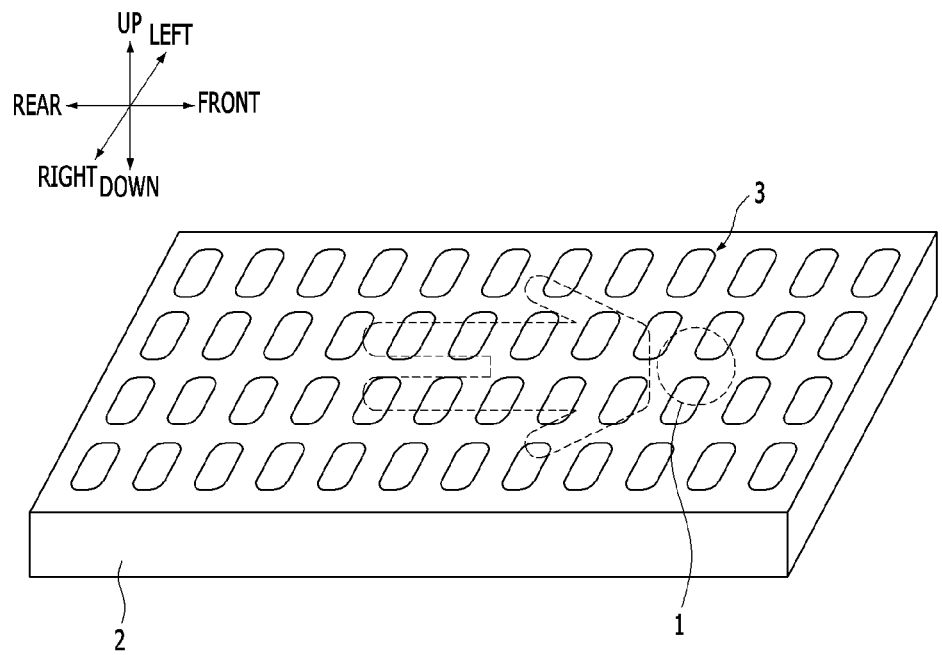
FIG. 9 is a view illustrating an example of a table considered in an image processing apparatus for a C-arm according to an exemplary embodiment of the present disclosure.

FIG. 9 is a view illustrating an example of a table 2 considered in an image processing apparatus 100 for a C-arm according to an exemplary embodiment of the present disclosure.

Referring to FIG. 9, on a top surface of the table 2 considered in the present apparatus 100, a plurality of pressure sensors 3 is disposed with intervals to acquire information about the length of the spine, among the physical feature information of the subject 1. At this time, the pressure sensor 3 is also referred to as a pressure sensitive sensor.

The analysis unit 140 analyzes a plurality of pressure sensing values acquired from the plurality of pressure sensors 3 to calculate the length of the spine as the physical feature information of the subject 1 located on the table 2.

The plurality of pressure sensors 3 is disposed on the top surface of the table 2 with intervals so that when the subject 1 lies on the top surface of the table 2, different pressure sensing values may be acquired from the plurality of pressure sensors 3 depending on the body structure (a body shape, a height, or the like) of the subject 1.

At this time, when a placement position of the plurality of pressure sensors 3 on the table 2 and ratio information between the plurality of pressure sensing values acquired from the plurality of pressure sensors 3 are used, a height of the subject 1 located on the top surface of the table 2 may be approximately estimated and thus the length of the spine of the subject 1 located on the top surface of the table 2 may also be estimated (inferred).

Accordingly, the analysis unit 140 analyzes the plurality of pressure sensing values acquired from the plurality of pressure sensors 3 to calculate ratio information (ratio) between the pressure sensing values acquired from the plurality of pressure sensors 3 in consideration of the placement information (disposed position information) of the plurality of pressure sensors 3.

Thereafter, the analysis unit 140 may calculate the length of the spine of the subject 1 as the physical feature information of the subject 1 from the ratio information (ratio) between the pressure sensing values calculated by analyzing the plurality of pressure sensing values, based on correlation information which has been stored in advance in a database unit 150.

In the database unit 150, correlation information obtained by analyzing a correlation between ratio information (ratio) between the plurality of pressure sensing values acquired from the plurality of pressure sensors 3, placement information (disposed position information) on the table 2 of the plurality of pressure sensors 3, and physical information of the subject (for example, information about a height, a gender, a weight, and a spine length of the subject) may be stored. At this time, the analysis of the correlation may be performed for a plurality of subjects (a plurality of users).

That is, in the database unit 150, correlation information (correlation analysis information) obtained by analyzing a correlation between "ratio information between the plurality of pressure sensing values, placement information of the plurality of pressure sensors, and the physical information of the subject" with respect to the plurality of subjects may be stored in advance.

At this time, the analyzed correlation information may be information derived by the learning using a deep learning model as an example. Here, the deep learning model may be an artificial intelligence (AI) algorithm model, a machine learning model, a neural network model (artificial neural network model), a neuro fuzzy model, and the like. Further, various neural network models which have been known in the related art or will be developed in the future, such as a convolution neural network (CNN), a recurrent neural network (RNN), or a deep neural network, may be applied as the deep learning model.

That is, the analysis unit 140 may calculate ratio information (ratio) between pressure sensing values by analyzing the plurality of pressure sensing values acquired from the plurality of pressure sensors 3 and calculate (infer or predict) a length of the spine, as physical feature information of the subject 1, from the previously calculated ratio information between the pressure sensing values, based on the correlation information which has been stored in advance in the database unit 150.

The length of the spine of the subject may vary depending on whether the height of the subject is 100 cm, 160 cm, or 180 cm. Generally, the longer the height of the subject, the longer the length of the spine. Such correlation information between the height of the subject and the length of the spine may also be included in the correlation information which has been stored in advance in the database unit 150.

According to this, there may be a difference in the positions of some pressure sensors which acquire the pressure sensing value among the plurality of pressure sensors 3 or a difference in the pressure sensing values of some pressure sensors, depending on the height of the subject. Accordingly, the analysis unit 140 may calculate the length of the spine of the subject 1 as physical feature information of the subject 1 located on the table 2, using an analysis result (for example, ratio information between pressure sensing values) of pressure sensing values acquired from the plurality of pressure sensors 3 and correlation information which has been stored in advance in the database unit 150.

At this time, the calculated length of the spine of the subject 1 for every subject may vary, depending on the subject, as described above. Therefore, the present apparatus 100 may set a predetermined route based on the length of the spine of the subject 1 calculated in the analysis unit 140.

Specifically, when the length of the spine of the subject 1 is calculated by analyzing the plurality of pressure sensing values, the present apparatus 100 may set a predetermined route by determining both end points of the spine portion corresponding to the calculated length of the spine as a starting point and an ending point of the predetermined route.

By doing this, as the different length of the spine is calculated for every subject 1, the predetermined route which is a movement route of the C-arm 200 whose movement is controlled by the movement control unit 110 may be set differently for each subject, based on the length of the spine of the subject 1 which is physical feature information of the subject 1 analyzed by the analysis unit 140.

Further, the analysis unit 140 performs the image analysis the projection image acquired by the image acquiring unit 120 to further determine a shape of the spine as the physical feature information of the subject 1. Here, the shape of the spine may refer to a curved shape of the spine. The analysis unit 140 may determine the position of the C-arm 200 with respect to the table 2, in consideration of the determined shape of the spine. Specifically, the analysis unit 140 may determine the position of the radiation generator 30 in the C-arm 200 with respect to the table 2, as the position of the C-arm 200, in consideration of the determined shape of the spine.

At this time, the predetermined route may be set (adjusted, corrected, or readjusted) to include the position of the C-arm 200 determined in consideration of the shape of the spine.

At this time, as the radiation generator 30 and the radiation detector 40 are fixedly provided at both ends of the C-arm frame 20, when the position of the radiation generator 30 is changed, the positions of the C-arm frame 20 and the radiation detector 40 may also be changed.

Hereinafter, with regard to determination of the position of the C-arm 200, as an example, it will be described based on determining the position of the radiation generator 30 for the convenience of description. However, it is not limited thereto but the determination of the position of the C-arm 200 may not only refer to the determination of the position of the radiation generator 30, but also refer to the determination of the position of the radiation detector 40, the determination of the position of the C-arm frame 20, or the determination of the position of the main body 10.

At this time, the position of the C-arm 200 determined by the analysis unit 140 may refer to the relative position (specifically, the relative position of the radiation generator) of the C-arm 200 with respect to the table 2.

Specifically, when the image acquiring unit 120 sequentially acquires the plurality of projection images, if a first projection image is acquired from the image acquiring unit 120, the analysis unit 140 may perform the image analysis the first projection image acquired from the image acquiring unit 120 to divide the first projection image into a first region and a second region.

At this time, the first region refers to a region corresponding to the spine (vertebra) and the second region may refer to a region excluding the first region.

Next, the analysis unit 140 may determine a curved shape of a rear end of the spine corresponding to the first region in the front and rear direction of the table 2 as a shape of the spine, based on the first region which is a region corresponding to the spine (vertebra) identified from the first projection image.

Next, the analysis unit 140 may determine the position of the C-arm 200 for acquiring the second projection image which is acquired subsequently to the first projection image, in consideration of the determined shape of the spine and an area of the second region other than the spine identified from the first projection image. A detailed description is as follows.

Figure 10:
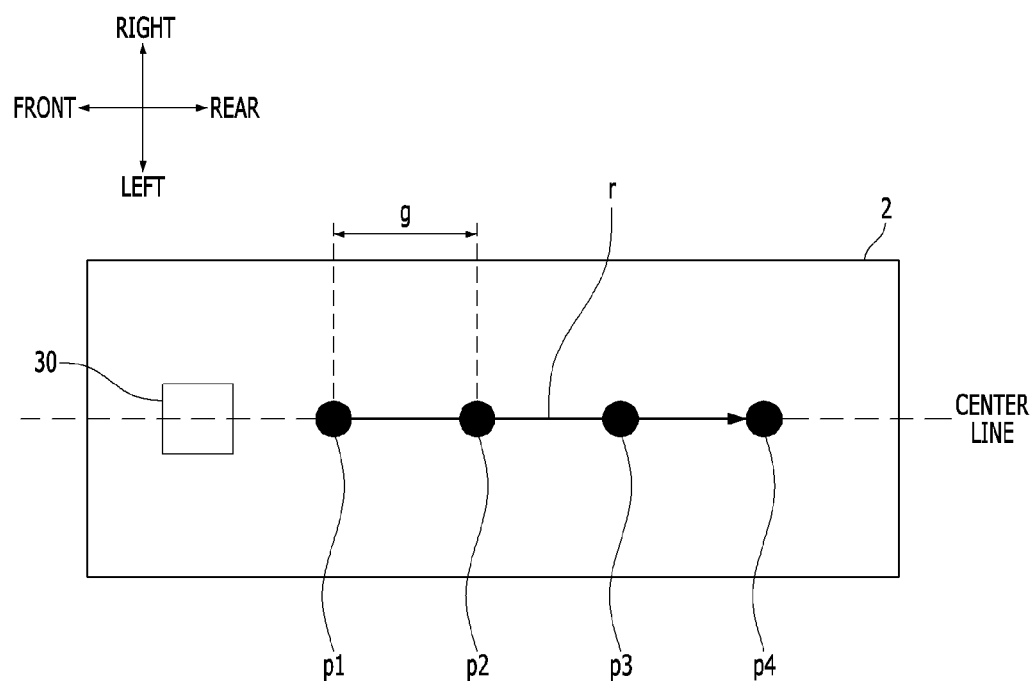
FIG. 10 is a view schematically illustrating an example that a radiation generator of a C-arm considered in an image processing apparatus for a C-arm according to an exemplary embodiment of the present disclosure moves along a predetermined route.

FIG. 10 is a view schematically illustrating an example that a radiation generator 30 of a C-arm 200 considered in an image processing apparatus 100 for a C-arm according to an exemplary embodiment of the present disclosure moves along a predetermined route r. Specifically, FIG. 10 is a view schematically illustrating a plan view when the table 2 is seen from an upper side.

Referring to FIG. 10, the predetermined route r may be set to allow the radiation generator 30 of the C-arm 200 to move along a front and rear direction of the table 2 with respect to a center line in the left and right direction of the table 2 as an example. That is, the movement control unit 110 may control the radiation generator 30 to move along a predetermined route r which is a straight route illustrated in FIG. 10 as an example.

At this time, the C-arm 200 may generate the projection image by irradiating the radiation at every predetermined interval g while moving along the predetermined route r. By doing this, for example, when the C-arm 200 generates a projection image at every predetermined interval g, the C-arm may generate projection images for a plurality of points p1, p2, p3, and p4 on the predetermined route r.

At this time, the interval between the plurality of points p1, p2, p3, and p4 is the predetermined interval g, which allows generation of a continuous (linear) panoramic image by connecting the projection images acquired at the plurality of points p1, p2, p3, and p4 as described above.

For example, a projection image (that is, a C-arm image) generated when the C-arm 200 is located at a first point p1 among the plurality of points may be the same as the first projection image I1 illustrated in FIG. 6. Further, a projection image generated when the C-arm 200 is located at a second point p2 may be the same as the second projection image I2 illustrated in FIG. 6 and a projection image generated when the C-arm 200 is located at a third point p3 may be the same as the third projection image I3 illustrated in FIG. 6. A projection image generated when the C-arm 200 is located at a fourth point p4 may be the same as the fourth projection image I4 illustrated in FIG. 6 as an example.

As described above, the present apparatus 100 controls the C-arm 200 to move along the predetermined route r to be horizontal with the table 2 in the front and rear direction of the table 2 and connects (matches, combines) the plurality of projection images I1, I2, I3, and I4 acquired from the C-arm 200 whose movement is controlled as described above. Therefore, as illustrated in the drawing at the bottom of FIG. 7, a single projection image for the entire spine of the subject 1 may be generated by a combined projection image T1 without having a distortion. The present apparatus 100 may provide the combined projection image T1 to be displayed on one screen by means of the display unit 50.

Figure 11:
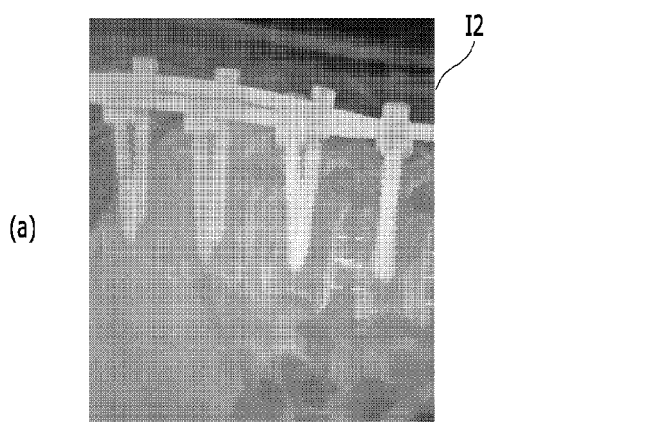
FIG. 11 is a view for explaining an example of acquiring an inappropriate projection image generated when a predetermined route is set as a simple straight route in an image processing apparatus for a C-arm according to an exemplary embodiment of the present disclosure.
Figure 11:
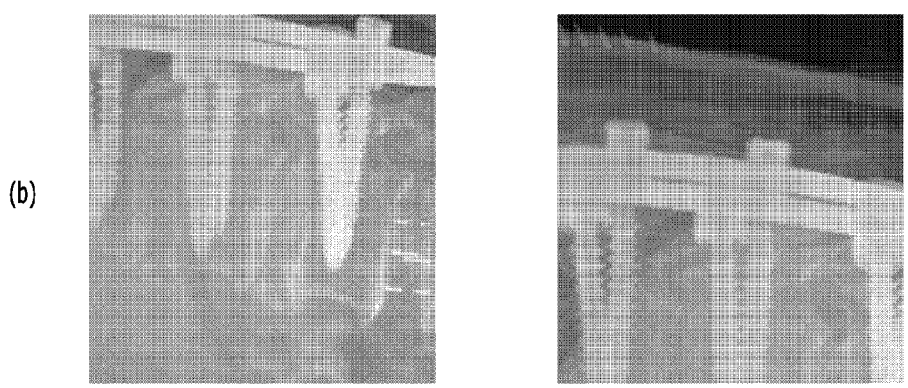

FIG. 11 is views for explaining an example of acquiring an inappropriate (abnormal) projection image generated when a predetermined route r is set as a simple straight route in an image processing apparatus for a C-arm according to an exemplary embodiment of the present disclosure.

Referring to FIG. 11, every subject 1 has some differences in the degree of the curvature of the spine or the position of the spine. However, for example, as illustrated in FIG. 10, the predetermined route r is simply set with respect to the position of the table 2 (that is, set as a straight route with respect to the center line of the table), at least some projection images among the plurality of projection images I1, I2, I3, and I4 acquired (generated) from the plurality of points p1, p2, p3, and p4 may not fully include the vertebra intended to be scanned, but include only a part of the vertebra (that is, a cut part).

For example, in the second image I2, the second image which is normally scanned (acquired) to fully include the vertebra intended to be scanned may be as illustrated in (a) of FIG. 11 as an example.

In contrast, the second image which is inappropriately scanned (acquired) due to wrong focusing caused by setting the predetermined route r to a simple straight route may be as illustrated in (b) of FIG. 11. That is, when the predetermined route r is set as only a simple straight route, as illustrated in (b) of FIG. 11, an image in which the corresponding vertebra to be scanned is not fully included, but is cut to include only a part thereof may be acquired.

As described above, when the abnormal projection image which is improperly focused like the image in (b) of FIG. 11 is acquired, the combined projection image is generated based on the abnormal projection image so that it is difficult to check the angle of the entire spine. Therefore, there is inconvenience to perform the re-scanning (reacquire the projection image). The re-scanning has a problem in that by the radiation exposure (radiation dose) to the subject 1 is increased and the operating hours are delayed to waist a lot of time and resources.

Therefore, according to the present disclosure, whenever the image acquiring unit 120 sequentially acquires the projection images from the C-arm 200, the analysis unit 140 performs the image analysis the acquired projection images and determines a position of the C-arm (a position of the C-arm to acquire a next projection image) to acquire a projection image subsequent to the analyzed projection image, in consideration of the curved shape of the rear end of the spine identified from the corresponding projection image by the image analysis and an area of the region other than the spine. Next, the predetermined route may be reset (adjusted) based on the determined position of the C-arm.

Figure 12:
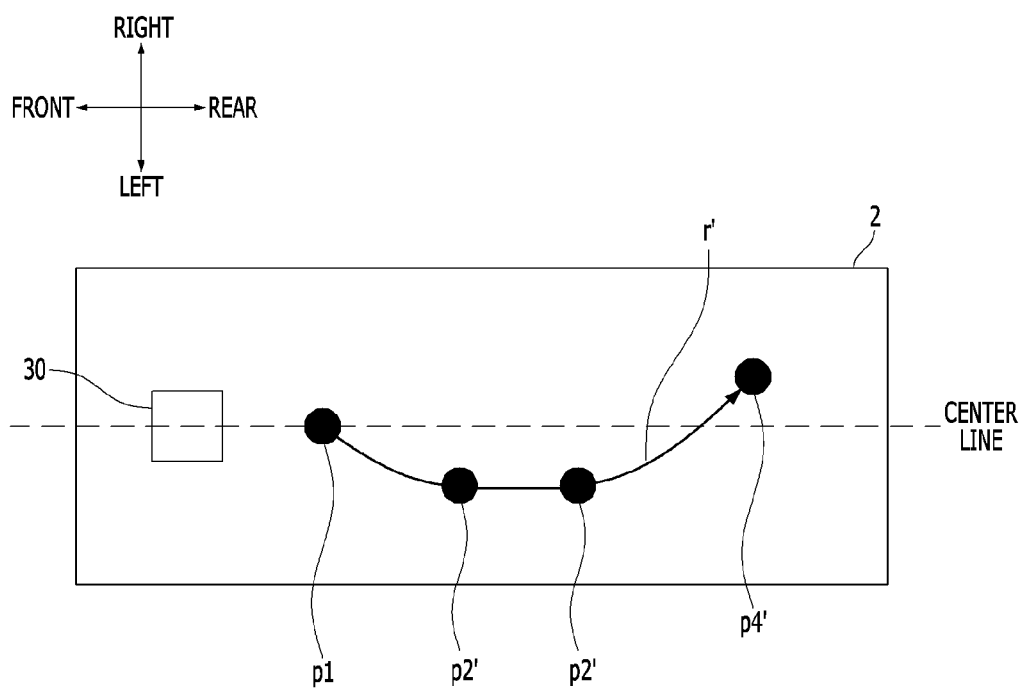
FIG. 12 is a view for explaining an example of determining a position of a C-arm for acquiring a projection image to be subsequently acquired by image analysis in an image processing apparatus for a C-arm according to an exemplary embodiment of the present disclosure and setting a predetermined route based on the determined position of the C-arm.

FIG. 12 is a view for explaining an example of determining a position of a C-arm for acquiring a projection image to be subsequently acquired by image analysis in an image processing apparatus for a C-arm according to an exemplary embodiment of the present disclosure and setting (adjusting) a predetermined route based on the determined position of the C-arm. That is, a predetermined route r' illustrated in FIG. 12 represents a route which is set (adjusted, reset) in consideration of the position of the C-arm determined based on the image analysis.

In the following description of the analysis unit 140, even though the contents described for the first projection image are omitted, the contents may be applied to the description of the other projection images (that is, the description of each of the plurality of projection images) in the same manner.

That is, referring to FIGS. 6 and 12, it is assumed that the image acquiring unit 120 acquires the first projection image I1 illustrated in FIG. 6 as a first projection image, from the C-arm 200. At this time, the analysis unit 140 may distinguish a first region corresponding to the spine (vertebra) from a second region other than the spine, by the image analysis for the first projection image I1.

Next, the analysis unit 140 may determine a curved shape of the rear end of the spine corresponding to the first region as a spine shape of the subject 1, based on the distinguished first region. At this time, as seen from the rear end (it means a part directed to a rear direction in the front and rear direction of the table) of the first projection image I1 illustrated in FIG. 6, it is confirmed that a curved shape of the rear end of the spine is slightly inclined toward a lower direction with respect to the drawing of FIG. 6.

Further, the analysis unit 140 may calculate the area of the corresponding second region based on the distinguished second region. In particular, the analysis unit 140 may calculate areas of one side and the other side of the distinguished second region with respect to an axial center of the spine corresponding to the first region. Here, for example, one side with respect to the axial center of the spine may refer to a part located above the axial center of the spine which is horizontally formed with respect to the drawing illustrated in FIG. 6. In contrast, the other side with respect to the axial center of the spine may refer to a part below the axial center of the spine with respect to the drawing of FIG. 6. In the following description, the area of one side in the second region may also be referred to as an area of a first sub region and the area of the other side in the second region may also be referred to as an area of a second sub region.

The analysis unit 140 may determine a position (a position of the radiation generator) of the C-arm 200 to acquire a second projection image which is a next second projection image which is acquired subsequently to the first projection image I1 in consideration of the shape of the spine (that is, the curved shape of the rear end of the spine) determined from the first projection image I1 and whether the area of the second region (specifically, the area of the first sub region and the area of the second sub region) satisfies a predetermined threshold area, At this time, it is assumed that the analysis unit 140 analyzes that the curve of the rear end of the spine in the first projection image I1 is slightly inclined toward the bottom and both the area of the first sub region and the area of the second sub region are equal to or larger than the predetermined threshold area. In this case, the analysis unit 140 may determine (reset or adjust) the position of the radiation generator 30 for acquiring the second projection image I2 to a second corrected point p2' which is located below the second point p2 which is located on the center line in FIG. 9 along the curved direction of the rear end of the spine and is also located below the first point p1.

Here, "below the second point p2" refers to a 6 o'clock direction with respect to the drawing of FIG. 12 and actually may refer to a left direction with respect to the table 2.

At this time, when both the area of the first sub region and the area of the second sub region are equal to or larger than the predetermined threshold area, it means that as the area of a background region (space) excluding a portion corresponding to the vertebra in the first projection image I1 is ensured by a predetermined amount, even though the radiation generator 30 slightly moves to the left/right/up/down direction with respect to the table 2, as illustrated in (b) of FIG. 11, a full projection image in a normal state may be acquired, rather than a projection image in which a part of the vertebra is cut.

As described above, when the analysis unit 140 determines the position of the second corrected point p2' as the position of the C-arm for acquiring the second projection image, the movement control unit 110 controls the radiation generator 30 of the C-arm 200 which acquires the first projection image I1 at the first point p1 to move to the position of the second corrected point p2'. Thereafter, the image acquiring unit 120 may acquire the second projection image generated by the C-arm 200 in the position of the second corrected point p2', from the C-arm 200.

At this time, it is assumed that the second projection image acquired in the position of the second corrected point p2' is the same as the second projection image I2 illustrated in FIG. 6. When the second projection image I2 is acquired, the analysis unit 140 performs the image analysis on the second projection image I2, similarly to the image analysis on the first projection image I1, and determines a position of the C-arm for acquiring a third projection image which is a third projection image acquired subsequently to the second projection image I2, based thereon.

At this time, it is assumed that the analysis unit 140 analyzes that the curve of the rear end of the spine in the second projection image I2 is a straight line parallel to the front and rear direction of the table 2, for example, as illustrated in FIG. 6 and both the area of the first sub region and the area of the second sub region in the second projection image I2 are equal to or larger than a predetermined threshold area. In that case, the analysis unit 140 may determine a position of a third corrected point p3' as illustrated in FIG. 12, as the position of the radiation generator 30 for acquiring the third projection image I3. That is, the analysis unit 140 may determine (reset, adjust) the position of the radiation generator 30 for acquiring the third projection image I3 to the third corrected point p3' which is located on the same line as the second corrected point p2' with respect to the front and rear direction along the curved direction (that is, the straight direction parallel to the front and rear direction) of the rear end of the spine in the second projection image I2 and is located below the third point p3 located on the center line in FIG. 10.

At this time, when both the area of the first sub region and the area of the second region in the second projection image I2 are equal to or larger than the predetermined threshold area, the position of the third corrected point p3' may be set to a position which is moved from the position of the second corrected point p2' by a predetermined distance to the 6 o'clock or 12 o'clock direction (that is, the left direction or the right direction with respect to the table) with respect to the drawing of FIG. 12.

If the area of the first sub region in the second projection image I2 is smaller than the predetermined threshold area, the analysis unit 140 recognizes that when the radiation generator 30 moves to the left direction (the 6 o'clock direction with respect to the drawing of FIG. 12) in the left and right direction with respect to the table 2 to acquire the third projection image, a projection image in which a part of the vertebra is cut is likely to be acquired to allow only the movement to the right direction, but limit the movement to the left direction from the position of the second corrected point p2'.

In contrast, if the area of the second sub region in the second projection image I2 is smaller than the predetermined threshold area (at this time, the area of the first sub region is equal to or larger than the predetermined threshold area), the analysis unit 140 recognizes that when the radiation generator 30 moves to the right direction (the 12 o'clock direction with respect to the drawing of FIG. 12) in the left and right direction with respect to the table 2 to acquire the third projection image, a projection image in which a part of the vertebra is cut is likely to be acquired to allow only the movement to the left direction, but limit the movement to the right direction from the position of the second corrected point p2'.

When the analysis unit 140 determines the position of the third corrected point p3' as the position of the C-arm for acquiring the third projection image, the movement control unit 110 moves the radiation generator 30 of the C-arm 200 which acquires the second projection image I2 at the second corrected point p2' to the position of the third corrected point p3'. Thereafter, the image acquiring unit 120 may acquire the third projection image generated by the C-arm 200 in the position of the third corrected point p3', from the C-arm 200.

At this time, it is assumed that the third projection image acquired in the position of the third corrected point p3' is the same as the third projection image I3 illustrated in FIG. 6. When the third projection image I3 is acquired, the analysis unit 140 performs image analysis on the third projection image I3 and determines a position of the C-arm for acquiring a fourth projection image which is a fourth projection image acquired subsequently to the third projection image I3 based thereon.

At this time, it is assumed that the analysis unit 140 analyzes that the curve of the rear end of the spine in the third projection image I3 is upwardly inclined toward an upper portion as illustrated in FIG. 6 and both the area of the first sub region and the area of the second sub region in the third projection image I3 are equal to or larger than a predetermined threshold area.

In that case, the analysis unit 140 may determine a position of a fourth corrected point p4' as illustrated in FIG. 12, as the position of the radiation generator 30 for acquiring the fourth projection image. That is, the analysis unit 140 may determine (reset, adjust) the position of the radiation generator 30 for acquiring the fourth projection image I4 to a fourth corrected point p4' located above the third corrected point p3', rather than the fourth point p4 located on the center line in FIG. 10 along the curved direction (that is, a curved shape upwardly inclined toward the upper portion) of the rear end of the spine in the third projection image I3.

At this time, in the example illustrated in FIG. 12, it is illustrated that the fourth corrected point p4' is located above the center line, but is not limited thereto. The movement degree from the position of the third corrected point p3' to the fourth corrected point p4' may be determined in consideration of the shape (a curved shape, a curvature degree, and a curved direction of the rear end of the spine) of the spine determined by image analysis on the third projection image and the area of the second region which is a region other than the spine.

As described above, when the position of the C-arm 200 for acquiring a next projection image acquired subsequently to the current projection image is determined after the image analysis on the current projection image acquired currently, the analysis unit 140 may determine the position of the C-arm 200 for acquiring the next projection image in consideration of not only the curved shape of the rear end of the spine in the current projection image, but also whether the area of the second region (specifically, the area of the first sub region and the area of the second sub region) as a region other than the spine is equal to or larger than the predetermined threshold area.

As the positions of the plurality of corrected points p2', p3', and p4' are determined, for example, the predetermined route r set as illustrated in FIG. 10 may be reset to a route r' including (via) the plurality of corrected points p2', p3', and p4' determined as illustrated in FIG. 12.

The present apparatus 100 determines the position of the C-arm for acquiring a projection image which is subsequently acquired by the image analysis and sets (readjusts) the predetermined route based on the determined position of the C-arm to effectively reduce the waste for the image acquired for an unnecessary region other than an intended scanning portion (a bone portion). That is, the present apparatus 100 may acquire a significant projection image (C-arm image) in which only an intended scanning portion (a bone portion) is focused, by setting (readjusting, correcting) the predetermined route based on the position of the C-arm.

The analysis unit 140 may determine the position of the C-arm 200 corresponding to each of the remaining projection images I2, I3, and I4 for acquiring the remaining projection images I2, I3, and I4 excluding the first projection image I1 among the plurality of projection images I1, I2, I3, and I4 acquired from the C-arm 200, after acquiring the first projection image I1 from the C-arm 200. At this time, a position of the C-arm 200 corresponding to any one projection image among the remaining projection images I2, I3, and I4 may be determined in consideration of the shape of the spine (specifically, a curved shape of the rear end of the spine) determined by the image analysis on the previous projection image acquired before any one projection image and an area (that is, the area of the second region) of the region other than the spine.

In other words, the position p2' of the C-arm (a position of the second corrected point) for acquiring the second projection image I2 among the remaining projection images I2, I3, and I4 may be determined based on the image analysis of the first projection image I1. Further, the position p3' of the C-arm (that is, a position of the third corrected point) for acquiring the third projection image I3 among the remaining projection images I2, I3, and I4 may be determined based on the image analysis of the second projection image I2.

The present apparatus 100 may automatically control the C-arm 200 to move along the predetermined route and control the C-arm 200 which moves along the predetermined route to automatically generate a projection image at every predetermined interval. At this time, the predetermined interval is an interval at which a continuous (linear) panoramic image may be generated so that the present apparatus 100 may acquire a single image as a combined projection image by which the entire spine of the subject 1 may be checked by combining the plurality of acquired projection images, by moving the C-arm 200 along the predetermined route only once (1 time).

The present apparatus 100 may generate the combined projection image which represents the entire spine of the subject 1 while minimizing the radiation exposure (radiation dose) to the subject 1 and more quickly acquire the combined projection image. The present apparatus 100 may display the generated combined projection image on one screen of the display unit 50. The present apparatus 100 may provide the combined projection image (that is, a linear panoramic projection image in which a plurality of projection images is connected) displayed on the display unit 50 to allow an operating surgeon to intuitively check an angle of the entire spine or a position of a desired spine of the subject 1.

The present apparatus 100 may acquire the combined image (that is, the combined projection image) for the entire spine of the subject 1 during the multilevel spinal surgery of the subject 1. When a problem occurs during the multilevel spinal surgery, the present apparatus 100 provides the combined projection image to allow the operating surgeon (an operator) to immediately identify the problem in the operating room and thus immediately correct the problem.

That is, the present apparatus 100 provides the combined projection image for the entire spine during the multilevel spinal surgery so that the problem is found in the operating room to be immediately corrected, thereby providing very great safety and convenience to both the doctor (operating surgeon) and the subject 1 (patient).

The C-arm of the related art has a limited sensor size (for example, a radiation detector having a size of 9 inches) so that it is difficult to acquire a projection image (a C-arm image) which represents the entire spine which is distributed (formed) to be long, like the vertebra as an example. Therefore, each of the projection images acquired from the C-arm have to be images for a partial spine portion representing only a part of the entire spine. The projection image acquired by the C-arm of the related art is accompanied by the difficulty in checking the angle of the entire spine or a position of the desired spine when the multilevel spinal surgery is performed.

Therefore, for example, the present apparatus 100 may generate a single combined projection image (that is, a linear panoramic image) by combining the plurality of projection images acquired from the C-arm 200 to display the projection image (C-arm image) for bones distributed over the long or wide area, like the spine, on one screen. According to the combined projection image, the entire spine may be intuitively recognized at a glance.

The image processing technique for a C-arm by the present apparatus 100 may be a technique for scanning (acquiring) a multilevel spine image to put an image of a long or wide bone, for example, like the vertebra in one screen. That is, the present disclosure proposes a technique for projecting (displaying) a multilevel spine image on one screen by introducing a panoramic photographic technique to the C-arm 200 of the related art by providing the present apparatus 100. That is, for example, the present apparatus 100 may provide the combined projection image to intuitively see a surgical site of the long segment like the spine (vertebra) at a glance.

Further, the image processing unit 130 may display the generated combined projection image on the display unit 50 of the C-arm 200. That is, the image processing unit 130 may display the generated combined projection image on one screen of the display unit 50 to be exposed.

At this time, when a user input is performed on any one point on the combined projection image displayed on the display unit 50, the image processing unit 130 recognizes any one point (that is, a point at which the user input is performed) corresponding to the user input as an abnormal portion (a portion on which a revision operation needs to be performed) in which a problem is sensed, to control the operation of a laser irradiating unit (not illustrated) provided at one end of the C-arm 200 to irradiate the laser in the position on a surface of a body of the subject 1 corresponding to any one point.

Here, for example, the laser irradiating unit (not illustrated) may be provided to be adjacent to the radiation generator 30, but is not limited thereto. Further, the user input is an input by an operating surgeon (operator) and for example, may refer to an input by touching a screen of the display unit 50 or clicking a mouse.

The present apparatus 100 irradiates the laser in a position on the surface of the body of the subject 1 corresponding to the portion on which the user input is performed to allow the laser to guide the operating surgeon (operator) to the position of the portion where a problem occurs during the multilevel spinal surgery on the subject 1.

The laser provided by the present apparatus 100 allows the operating surgeon to intuitively recognize the position of the portion where the problem occurs and thus, allows the corresponding portion where the problem occurs to be quickly and easily re-operated or corrected.

The present apparatus 100 may set the predetermined route customized for each of the subjects 1, which is a route on which the C-arm 200 moves in consideration of the physical feature information (a length of the spine or a shape of the spine) and thus, efficiently generate and provide the continuous panoramic image which is a combined projection image customized for each of the subject 1.

Hereinafter, an operation flow of the present disclosure will be described in brief based on the above detailed description.

Figure 13:
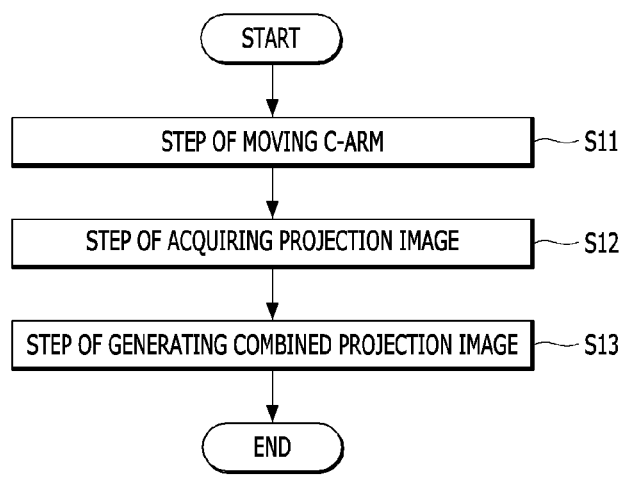
FIG. 13 is a flowchart of an operation of a control method of an image processing apparatus for a C-arm according to an exemplary embodiment of the present disclosure.

FIG. 13 is a flowchart of an operation of a control method of an image processing apparatus for a C-arm according to an exemplary embodiment of the present disclosure.

The control method of an image processing apparatus for a C-arm illustrated in FIG. 13 may be performed by the present apparatus 100 (the image processing apparatus for a C-arm) described above. Therefore, even though some contents are omitted below, the contents which have been described for the present apparatus 100 (the image processing apparatus for a C-arm) may be applied to the description for the control method of an image processing apparatus for a C-arm in the same manner.

Brief description will be made with reference to FIG. 13. In step S11, the movement control unit moves the C-arm which irradiates radiation onto a bone of the subject located on the table and detects the radiation which penetrates the bone to generate a projection image for the bone, along the predetermined route.

Next, in step S12, the image acquiring unit may acquire a plurality of projection images which is generated at every predetermined interval by the C-arm which moves in accordance with the movement control of the movement control unit in step S11, from the C-arm. At this time, when the image acquiring unit acquires the plurality of projection images from the C-arm, the image acquiring unit may sequentially acquire the projection image whenever the projection image is generate by the C-arm.

At this time, the predetermined interval may be an interval at which a continuous panoramic image may be generated by connecting the plurality of projection images acquired from the C-arm.

Next, in step S13, the image processing unit may generate a combined projection image obtained by combining a plurality of projection images acquired in step S12 as a single image. At this time, the combined projection image is one image in which the plurality of projection images acquired from the C-arm is entirely connected and is also referred to as a linear panoramic image (a linear panoramic projection image).

Further, even though not illustrated in the drawing, the control method of the image processing apparatus for a C-arm according to the exemplary embodiment of the present disclosure may further include a step of analyzing physical feature information of the subject in the analysis unit (hereinafter, for the convenience of description, referred to as a step S1), before the step S11.

At this time, in step S1, the analysis unit may calculate the length of the spine as physical feature information of the subject by analyzing a plurality of pressure sensing values acquired from the plurality of pressure sensors. Next, the predetermined route considered in step S11 may be set to be different depending on the physical feature information of the subject analyzed by the analysis unit in step S1.

Further, the control method of the image processing apparatus for a C-arm according to the exemplary embodiment of the present disclosure may further include a step of determining a shape of the spine as the physical feature information of the subject by analyzing the projection image acquired from the image acquiring unit, by the analysis unit and determining a position of the C-arm with respect to the table in consideration of the determined shape of the spine (hereinafter, for the convenience of description, referred to as a step S12-1), after the step S12 (or before step S13).

At this time, the predetermined route considered in step S11 may be set (reset, corrected, readjusted) to include the position of the C-arm determined in step S12-1.

Further, the control method of the image processing apparatus for a C-arm according to the exemplary embodiment of the present disclosure may further include a step of displaying the combined projection image generated by the image processing unit on a display unit, after the step S13.

Further, when a user input is performed on any one point on the combined projection image displayed on the display unit, after the displaying, the control method of the image processing apparatus for a C-arm according to the exemplary embodiment of the present disclosure may further include a step of controlling an operation of a laser irradiating unit provided at one end of the C-arm to irradiate laser onto a position on a surface of a body of the subject corresponding to any one point.

In the above-description, steps S11 to S13 may be further divided into additional steps or combined as smaller steps depending on an implementation example of the present disclosure. Further, some steps may be omitted if necessary and the order of steps may be changed.

The control method of an image processing apparatus for a C-arm according to the exemplary embodiment of the present disclosure may be implemented as a program command which may be executed by various computers to be recorded in a computer readable medium. The computer readable medium may include solely a program instruction, a data file, and a data structure or a combination thereof. The program instruction recorded in the medium may be specifically designed or constructed for the present disclosure or known to those skilled in the art of a computer software to be used. Examples of the computer readable recording medium include a magnetic media such as a hard disk, a floppy disk, or a magnetic tape, an optical media such as a CD-ROM or a DVD, a magneto-optical media such as a floptical disk, and a hardware device which is specifically configured to store and execute the program instruction, such as a ROM, a RAM, and a flash memory. Examples of the program instruction include not only a machine language code which is created by a compiler but also a high level language code which may be executed by a computer using an interpreter. The hardware device may operate as one or more software modules in order to perform the operation of the present disclosure and vice versa.

Further, the control method of an image processing apparatus for a C-arm may also be implemented as a computer program or an application executed by a computer which is stored in a recording medium.

The above-description of the present disclosure is illustrative only and it is understood by those skilled in the art that the present disclosure may be easily modified to another specific type without changing the technical spirit or an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

What is claimed is:

1. An image processing apparatus for a C-arm, comprising:
   a movement control unit which moves a C-arm which irradiates a radiation onto a bone of a subject located on a table and detects the radiation which penetrates the bone to generate a projection image for the bone, along a predetermined route, wherein the predetermined route is a route set to move the C-arm along a front and rear direction of the table;
   an image acquiring unit which acquires a plurality of projection images generated by the moving C-arm at every predetermined interval;
   an analysis unit which analyzes physical feature information of the subject located on the table; and
   an image processing unit which generates a combined projection image in which the plurality of acquired projection images is combined,
   wherein the predetermined route is set to be different depending on the physical feature information of the subject which is analyzed by the analysis unit, and
   wherein the predetermined interval is an interval at which a continuous panoramic image is generated by connecting the plurality of acquired projection images.

2. The image processing apparatus for a C-arm according to claim 1, wherein a size of the projection image is determined by a size of a radiation detector which is provided at one end of the C-arm to detect radiation which penetrates the bone and a size of the combined projection image is larger than a size of each of the plurality of projection images.

3. The image processing apparatus for a C-arm according to claim 1, wherein a plurality of pressure sensors is disposed on a top surface of the table with an interval and the analysis unit calculates a length of a spine as the physical feature information of the subject by analyzing a plurality of pressure sensing values acquired from the plurality of pressure sensors.

4. The image processing apparatus for a C-arm according to claim 1, wherein the analysis unit further determines a shape of a spine as the physical feature information of the subject by analyzing the projection image acquired by the image acquiring unit and determines a position of the C-arm with respect to the table in consideration of the determined shape of the spine and the predetermined route is set to include the determined position of the C-arm.

5. The image processing apparatus for a C-arm according to claim 4, wherein the analysis unit determines a curved shape of a rear end of the spine corresponding to a first region for a front and rear direction of the table as the shape of the spine, based on the first region which is a region corresponding to the spine identified from a first projection image by analyzing the first projection image acquired by the image acquiring unit and determines the position of the C-arm for acquiring a second projection image acquired subsequently to the first projection image in consideration of the determined shape of the spine and an area of a second region which is a region other than the spine identified from the first projection image.

6. The image processing apparatus for a C-arm according to claim 4, wherein the analysis unit determines a position of the C-arm corresponding to each of remaining projection images for acquiring the remaining projection images other than a first projection image among the plurality of projection images and
   the position of the C-arm corresponding to any one projection image among the remaining projection images is determined in consideration of a shape of a spine determined by an image analysis of a previous projection image acquired before any one projection image and an area of a region other than a spine.

7. The image processing apparatus for a C-arm according to claim 1, wherein the image processing unit displays the generated combined projection image on a display unit and when a user input is performed on any one point on the combined projection image displayed on the display unit, controls an operation of a laser irradiating unit provided at one end of the C-arm to irradiate laser onto a position on a surface of a body of the subject corresponding to any one point.

8. An image processing apparatus for a C-arm, comprising:
   a movement control unit which moves a C-arm which irradiates a radiation onto a bone of a subject located on a table and detects the radiation which penetrates the bone to generate a projection image for the bone, along a predetermined route;
   an image acquiring unit which acquires a plurality of projection images generated by the moving C-arm at every predetermined interval; and
   an image processing unit which generates a combined projection image in which the plurality of acquired projection images is combined, wherein the predetermined interval is an interval at which a continuous panoramic image is generated by connecting the plurality of acquired projection images, and wherein the image processing unit displays the generated combined projection image on a display unit and when a user input is performed on any one point on the combined projection image displayed on the display unit, controls an operation of a laser irradiating unit provided at one end of the C-arm to irradiate laser onto a position on a surface of a body of the subject corresponding to any one point.

\* \* \* \* \*